United States Patent [19]

Kline

[11] Patent Number: 5,384,241

[45] Date of Patent: Jan. 24, 1995

[54] SPECIFIC BINDING ASSAY COMPOUND WITH INHIBITIVE SELF-QUENCHING CHARACTERISTICS

[75] Inventor: Stanley Kline, Brooklyn, N.Y.

[73] Assignee: Enzo Diagnostics, Inc., Farmingdale, N.Y.

[21] Appl. No.: 443,812

[22] Filed: Nov. 29, 1989

Related U.S. Application Data

[63] Continuation of Ser. No. 96,182, Sep. 11, 1987, abandoned.

[51] Int. Cl.$^6$ .................... C07H 21/00; G01N 33/53; C12Q 1/68

[52] U.S. Cl. ................................. 435/6; 536/25.32; 536/1.11; 435/7.1; 435/968; 436/544; 436/545; 436/546; 436/800; 436/805; 436/827; 436/828; 530/802; 530/391.3

[58] Field of Search .................... 435/6, 968, 7.1; 436/546, 544, 545, 800, 805, 827, 828; 536/124, 27, 25.32, 1.11; 530/389, 802

[56] References Cited

U.S. PATENT DOCUMENTS

| | | | |
|---|---|---|---|
| 3,996,345 | 12/1976 | Ullman et al. | 424/12 |
| 4,134,792 | 1/1979 | Boguslaski et al. | 195/99 |
| 4,166,105 | 8/1979 | Hirschfeld | 436/800 |
| 4,213,893 | 7/1980 | Carrico et al. | 260/112.5 |
| 4,230,797 | 10/1980 | Boguslaski et al. | 435/7 |
| 4,238,195 | 12/1980 | Boguslaski et al. | 23/230 B |
| 4,302,204 | 11/1981 | Wahl et al. | 23/230.3 |
| 4,318,980 | 3/1982 | Boguslaski et al. | 435/7 |
| 4,318,981 | 3/1982 | Burd et al. | 435/7 |
| 4,318,982 | 3/1982 | Hornby et al. | 435/7 |
| 4,358,535 | 11/1982 | Falkow et al. | 435/5 |
| 4,395,486 | 7/1983 | Wilson et al. | 435/6 |
| 4,442,204 | 4/1984 | Greenquist et al. | 435/7 |
| 4,452,886 | 6/1984 | Henry | 436/546 |
| 4,492,751 | 1/1985 | Boguslaski et al. | 435/7 |
| 4,556,643 | 12/1985 | Paau et al. | 436/501 |
| 4,563,417 | 1/1986 | Albarella et al. | 435/6 |
| 4,581,333 | 4/1986 | Kourilsky et al. | 435/6 |
| 4,748,111 | 5/1988 | Dattagupta et al. | 436/518 |
| 4,849,513 | 7/1989 | Smith et al. | 536/27 |
| 4,876,335 | 10/1989 | Yamane et al. | 536/27 |
| 5,093,232 | 3/1992 | Urdea et al. | 435/6 |
| 5,118,800 | 6/1992 | Smith et al. | 536/23 |

FOREIGN PATENT DOCUMENTS

| | | |
|---|---|---|
| 1124643 | 6/1985 | Canada . |
| 0070685 | 1/1983 | European Pat. Off. . |
| 0070687 | 1/1983 | European Pat. Off. . |
| 0140521 | 5/1985 | European Pat. Off. . |
| 0063879 | 11/1989 | European Pat. Off. . |

OTHER PUBLICATIONS

Haralambidis, et al., *Nuc. Acids Research*, vol. 15, No. 12, pp. 4856–4876, (1987).

Visor, et al, *Journal of Pharmaceutical Sciences*, vol. 70, No. 5 pp. 469–475 (1981).

Soini, et al, *Clin. Chem.*, vol. 25, No. 3 pp. 353–361 (1979).

Exley, et al., *J. Steroid Biochem.*, vol. 14 pp. 1297–1302 (1981).

Richardson, et al., *Nuc. Ac. Res.*, vol. 11, No. 18, pp. 6167–6184 (1983).

Hemmila, *Clin. Chem.*, vol. 31, No. 3, pp. 359–370 (1985).

Hassan, et al, *FEBS Letters*, vol. 103, No. 2, pp. 339–341 (1979).

Haralambidis, J., et al., Chemical Abstracts, vol. 108 (21), abstract No. 187182z (1987).

*Primary Examiner*—Toni R. Scheiner
*Attorney, Agent, or Firm*—Ronald C. Fedus

[57] ABSTRACT

Disclosed is an assay system including a compound comprising an analyte-specific moiety having substituted thereon a polymer comprising plurality of self-quenching emitter moieties and a plurality of iso-charged functionality separating the emitter moieties. The present invention provides compounds that overcome the undesirable effects of self-quenching when multiple emitter moieties are used for labelling of assay reagents. Avoidance of this self-quenching phenomenon by the compounds of the invention makes it possible to introduce a more concentrated degree of labelling on to analyte-specific molecules such as oligo nucleotide probes, antibodies and other specific binding proteins and analyte-specific polysaccharides. Therefor, it is possible to effect greater assay sensitivity because the number of labels per recognition molecule(analyte-specific moiety) can be increased beyond the point previously possible without the reduction in signal caused by self-quenching.

13 Claims, No Drawings

SPECIFIC BINDING ASSAY COMPOUND WITH INHIBITIVE SELF-QUENCHING CHARACTERISTICS

This is a continuation of application Ser. No. 07/096,182 filed Sept. 11, 1987, now abandoned.

BACKGROUND OF THE INVENTION

1) Field of the Invention

This invention relates to signal generating systems for specific binding assays. More particularly, it relates to the enhancement of available signal by reduction in self-quenching of signal moieties associated with the assay systems.

2) Brief Description of the Prior Art

The development of specific binding assay techniques has provided extremely useful analytical methods for determining various substances of diagnostic, medical, environmental and industrial importance which appear in liquid media at very low concentrations. Specific binding assays are based on the specific interaction between a bindable analyte under determination, and a binding partner therefor, i.e., analyte-specific moiety. The binding of the analyte-specific moiety and interaction of any additional reagents, if necessary, effect a mechanical separation of bound and unbound labeled analyte or affect the label in such a way as to modulate the detectable signal. The former situation is normally referred to as heterogeneous and the latter as homogeneous, in that the latter technique does not require a separation step. Where one of the analyte and its binding partner is a hapten or antigen and the other is a corresponding antibody, the assay is known as an immunoassay. See, generally, Odell and Daughaday (Eds.), *Principles of Competitive Protein-Binding Assays*, J. B. Lippincott Co., Philadelphia (1971). Where one of the analyte and its binding partner is a target nucleic acid sequence and the other is a complementary nucleic acid sequence, the assay is known as a nucleic acid hybridization assay. See, generally, Falkow, et.al., U.S. Pat. No.4,358,535, Kourilsky, et. al., U.S. Pat. No. 4,581,333, Albarella, et. al., U.S. Pat. No. 4,563,417 and Paau, et. al. U.S. Pat. No. 4,556,643. In conventional label conjugate specific binding assay techniques, a sample of the liquid medium to be assayed is combined with various reagent compositions. Such compositions include a label conjugate comprising a binding component incorporated with a label. The binding component in the conjugate participates with other constituents, if any, of the reagent composition and the ligand in the medium under assay to form a binding reaction system producing two species or forms of the conjugate, e.g., a bound-species (conjugate complex) and a free-species. In the bound-species, the binding component of the conjugate is bound by a corresponding binding partner whereas in the free species, the binding component is not so bound. The amount or proportion of the conjugate that results in the bound species compared to the free species is a function of the presence (or amount) of the analyte to be detected in the test sample. An alternative format for specific binding assays is the "sandwich" or "capture" assay in which the target analyte is bound between a first specific binding partner, which can be directly or indirectly fixed to a solid matrix, and a second specific binding partner, which is associated with a signal generating or labeling system.

Early hybridization techniques involved the use of radioactive labels such as $H^3$, $P^{32}$, or $I^{123}$. An alternative is disclosed in British Patent No. 2,019,408 which describes polynucleotide probes labeled with biotin through cytochrome C linkage groups. Bound probes are detectable by enzyme-labeled avidin through a chromogenic reagent signalling system. An improved approach to labeling probes with low molecular weight analytes, such as biotin, is described in European Patent Application No. 63,879. In this technique, 5-allylamine-deoxyuridine triphosphate (dUTP) derivatives are condensed with the desired analyte label in a manner which is not disruptive of hybridization. The thus modified nucleotide is incorporated by standard enzymatic methods into the desired oligo- or polynucleotide probe. The use of light emitting labels is reported in European Patent Application Nos. 70,685 and 70,687. Other representative patent literature pertaining to hybridization assays includes U.S. Pat. Nos. 4,302,204 concerning the use of certain water soluble polysaccharides to accelerate hybridization on a solid phase; 4,358,535 concerning the detection of pathogens in clinical samples; and 4,395,486 concerning the detection of the sickle cell anemia trait using a synthetic oligonucleotide probe.

Labeling systems for protein binding or immunoassay type specific binding assay systems are numerous and well known in the art. A review of many such labeling systems is presented by U.S. Pat. Nos. 4,134,792; 4,213,893; 4,230,797; 4,238,195; 4,318,980; 4,318,981; 4,318,982; 4,442,204, 4,492,751 and EPO 140,521.

Visor, et. al., *J. Pharm. Sci.*, 70:469(1981) also provides an overview and literature survey regarding fluorescent immunoassay. Another of many review articles published is Soini, et.al., *Clin. Chem.*, 25:353(1979). Exley, et.al., *J. Steroid Biochem.*, 14:1297(1981) reports an immunoassay using a poly-L-lysine carrier to which are attached multiple fluoresceins. Attachment of fluorescein to oligonucleotides has also been reported. See Richardson, et.al., *Nuc. Acids Res.*, 11:6167(1983) and the literature cited therein. Various refinements and improvements of this basic fluorescent specific binding assay technology have evolved.

Fluorescent binding assays of the homogeneous type have been reported which avoid the usually disadvantageous separation step. One such method is based on quenching or enhancement of fluorescence upon binding of a fluorescer-ligand conjugate with its target binding partner(analyte). Examples are provided in Belgian Patent No. 858,722 and German Offenlegungsschriften Nos. 2,716,276 and 2,716,515. A variation of this assay method is described in U.S. Pat. No. 3,996,345 which employs a specific quenching substance as a counterpart to the fluorescer label. These methods are reviewed in Visor, et. al. and Soini, et. al., supra.

Hemmilia, *Clin. Chem.* 31:359(1985) provides a more recent review of fluoroimmunoassays and immunofluorimetric assays. It notes that the close proximity of two fluorescent probes in a protein can cause self-quenching if their absorption and emission spectra overlap. It also states that despite their short Stokes' shift and consequent sensitivity to concentration quenching, polymeric fluorescein labels have also been used. Hassan, et. al., *FEBS Letters* 103:339(1979) is cited. Also mentioned is that self-quenching can be eliminated by introducing releasable linkages to polymeric labels. The quenched, polymer-bound probes are hydrolyzed in a solution of monomeric fluorescent dye once the immunoreaction is complete. Yaverbaum, et. al., U.S. Pat. No. 4,576,912 is cited.

Hassan, et. al., supra, addresses the "concentration quenching" of fluorescein in multi-substituted polymers. As illustrated in FIG. 1 thereof, an excess of antifluorescein antibodies is added to the multi-fluorescein substituted polymer. The remaining unoccupied antibody sites are "back-titrated" by addition of a monomeric fluorescein reagent. The monomeric fluorophores which become antibody-bound are also efficiently quenched, while the remander give a fluorescent signal related to the number of fluoresceins on the polymer but unquenched because the fluorescence is produced by these conventional monomeric units in solution and not by those of the multi-fluoresceinated polymer. In fact, complete quenching, intentionally, of the multi-fluoresceinated polymer is the result.

Thus, the disadvantageous characteristic of fluorescent molecules to emit diminished signal when in high concentrations or close proximity has been addressed by resort to alternative label systems or conversion of multifluoresceinated label systems to ones in which signal is read from conventional fluorescein polymers.

SUMMARY OF THE INVENTION

The present invention provides an assay system employing compounds that overcome the undesirable effects of self-quenching when multiple emitter moieties are used for labeling of assay reagents. Avoidance of this self-quenching phenomenon by the compounds of the invention makes it possible to introduce a more concentrated degree of labeling onto analyte-specific molecules and using such labeling for direct signal detection. As a result, it is possible to effect greater assay sensitivity, because the number of labels per recognition molecule(analyte-specific moiety) can be increased beyond the point previously possible without the reduction in signal caused by self-quenching or resort to secondary, monomeric signal generation.

Accordingly, the invention provides an assay system and compound comprising an analyte-specific moiety having substituted thereon a plurality of self-quenching emitter moieties and a plurality of isocharged functionalities separating the emitter moieties. In one aspect the emitter moiety is bound to the analyte-specific moiety through a linkage group, the isocharged functionality can be a component of the linkage group and, when it is, it is preferably in close proximity to the emitter moiety. In another aspect, the isocharged functionality is bound to the analyte-specific moiety directly or through a linkage group, for instance DNA. In this aspect the analyte-specific moiety clearly has substituted thereon a sequence of emitters and isocharged functionalities.

The isocharged functionalities can provide either a negative or positive charge but will be one or the other on any given compound. By being associated with the emitter moiety, either by being in close proximity or being positioned between emitter moieties, the like charges of the isocharged functionalities repel each other and the emitter moieties are thereby spaced apart. When spaced apart in this manner, the emitter moieties are unable to affect the degree of energy emitted by their neighbors, i.e., quenching.

DETAILED DESCRIPTION OF THE INVENTION

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated by this term as used and can be assayed in accordance with the invention.

The term "analyte" refers to any substance, or class of related substances, whose presence is to be qualitatively or quantitatively determined in a sample fluid. The present assay can be applied to the detection of analytes for which there is a specific binding partner and, conversely, to the detection of the capacity of an analyte medium to bind an analyte (usually due to the presence of a binding partner for the analyte in the sample). The analyte usually is an oligo- or polynucleotide, peptide, protein, carbohydrate, glycoprotein, steroid, or other organic molecule for which a specific binding partner exists or can be provided by immunological or synthetic means. The analyte, in functional terms, is usually selected from an RNA or DNA for which a complementary nucleic acid sequence exists or can be prepared; antigens and antibodies thereto; haptens and antibodies thereto; and hormones, vitamins, metabolites and pharmacological agents and their receptors and binding substances.

The term "analyte-specific moiety" refers to any compound or composite capable of recognizing a particular spatial and polar organization of a molecule, i.e., epitopic site, or a particular informational sequence such as a nucleic acid sequence in preference to other substances. In the majority of embodiments the analyte-specific moiety will be a specific binding assay reagent, such as a nucleic acid hybridization assay probe or a polyclonal or monoclonal antibody or other specific binding protein. In another aspect, the analyte-specific moiety can be a lectin which binds preferentially to a specific saccharide. Examples of particular interest include DNA hybridization assay oligonucleotide probes, such as those specific for disease-causing organisms, e.g., $N.$ $gonorrhoeae$ or human papilloma virus, or genetic disorders, e.g., Tay-Sachs' or Down's syndrome.

The analyte-specific moiety is attached directly or through a non-interfering linkage group with other moieties. When attached directly, such attachment can be by covalent attachment or noncovalent binding. When it is attached through a non-interfering linkage group, this non-interfering linkage group is one which does not substantially interfere with the characteristic ability of the analyte-specific moiety to bind with its binding partner analyte. Further, such linkage groups are characterized in that they do not substantially interfere with the energy emission or other detectable characteristics of an emitter moiety to which they are attached. The linkage group can be uncharged or can include one or more isocharged functionalities.

Examples of uncharged linkage groups include homopolymeric or heteropolymeric backbones, including polymeric alkyls. Such uncharged linkage groups can include one or more polyhydroxyls, such as polyethylene glycol, polythiols, polyacrylates or oxiranes. Naturally charged linkage groups which can advantageously be used include nucleic acid sequences, polycarboxylates and polyamines.

The "self-quenching emitter moiety" of the invention is one which releases energy in a detectable form and in which the relative amount of such energy released per moiety is reduced in relation to the number and proximity of other like moieties. The self-quenching emitter moiety can be attached directly to the analyte-specific moiety, forming a portion of a linkage group to which a self-quenching emitter moiety is attached or attached to an uncharged linkage group by the self-quenching emitter moieties. Exemplary of such moieties are fluorescent substances such as fluorescein and the like.

The "isocharged functionalities" are of a polarity and charge intensity sufficient, in view of the proximity in which they are positioned, to maintain a distance between them and to likewise maintain a distance between self-quenching emitter moieties. The isocharged functionalities can be of a positive or negative charge. Examples of positively charged functionalities include amines, chelated metals or other positively charged species. Examples of negatively charged species include carboxyl, phosphate or sulfate groups. Alternatively, the natural negative charge of nucleic acid sequences can be used to such advantage when emitter moieties are appropriately positioned with respect to the phosphate moieties of the mononucleotides in a nucleic acid sequence, such as a hybridization probe.

In one aspect of the invention, the analyte-specific moiety is substituted along its length by an alternating sequence of emitters and isocharged functionalities and is characteristically a polymer of individual monomeric units such as nucleotides, amino acids or saccharides which have been substituted with self-quenching emitter moieties and isocharged functionalities either before or after polymer formation.

In another aspect of the invention, the analyte-specific moiety is substituted by a series of linkage groups, each of which carries an emitter moiety and is substituted along its length by a plurality of charged functionalities. As noted above, the charge on each linkage group will be the same so as to cause them and the emitter moieties thereon to be appropriately spaced apart. In another embodiment of this aspect, the analyte specific moiety is provided with a series of linkage groups each of which has, in alternating sequence along its length, a plurality of emitter moieties and therebetween charged functionalities which, as before, cause such linkage groups to be appropriately spaced apart.

In yet another aspect, a plurality of linkage groups is attached to the analyte specific moiety and each is provided with a plurality of isocharged moieties. Between such linkage groups are linkage groups carrying emitter moieties, thereby forming an alternating sequence of linkage groups carrying emitter moieties and those which do not. In this aspect the linkage groups which are not provided with emitter moieties carry a plurality of charged functionalities and, optionally, those linkage groups with such emitter moieties can also be similarly charged.

The following examples illustrate but are not a limitation of the present invention.

EXAMPLE 1

In the experiments reported by this example a number of fluoresceinated polymers characterized by either charged or uncharged backbones are compared. The fluorescence of each relative to unbound 6-carboxyfluorescein is measured to ascertain the effect of polymer backbone and charge on fluorescence.

Fluoresceinated Polyethyleneimine

Fluoresceinated dsDNA is prepared as follows. Polyethyleneimine (average m.w. 1,400; 400 $\mu$g, 2 $\mu$m amine) and 6-carboxyfluorescein-N-hydroxysuccinimide ester (f-NHS) (2.7 mg, 6.0 $\mu$mol) are reacted in 0.1M sodium borate (0.3 ml) for 4 hours at room temperature. The precipitate is collected and purified by repeatedly dissolving in dimethylformamide (DMF) and acetic acid and reprecipitation with acetone. The resultant fluoresceinated compound is substantially electrically neutral.

Fluoresceinated dsDNA

Here, 5-(3-aminopropenyl)-deoxyuridine is substituted for thymidine in double stranded DNA(dsDNA) of plasmid source using a nick translation protocol. The amine substituted dsDNA is purified by phenol extraction and G-25 chromatography. An aliquot (100 $\mu$g) of this dsDNA is heat denatured and reacted with f-NHS (0.56 mg, 1.5 $\mu$mol) dissolved in dimethylformamide(DMF) (12.51 $\mu$l) for 4 hours at room temperature. The fluoresceinated dsDNA is alcohol precipitated, chromatographed twice on G-25 and alcohol precipitated a second time. The product has an average length of 200 base pairs and contains 5 fluorescein molecules per 100 bases.

Fluoresceinated Bovine Serum Albumin

Bovine serum albumin (BSA) (1 mg) dissolved in 0.1M sodium borate (1 ml) is reacted with f-NHS (2.7 mg; 60 $\mu$mol) dissolved in DMF (100 $\mu$l). After 4 hours, the reaction is exhaustively dialyzed into 10 mM sodium bicarbonate with 4 changes of buffer. Silica gel thin layer chromatography reveals no unbound fluorescein upon elution with 30% methanol: chloroform.

Fluoresceinated ssDNA

A single stranded oligodeoxynucleotide(ssDNA) containing 5-(3-aminopropenyl)-deoxyuridine at position 13 (relative to the 5' end) is synthesized using an Applied Biosystems Synthesizer. The ssDNA oligomer is purified by reverse phase chromatography and polyacrylamide gel electrophoresis. The purified ssDNA oligomer (75 $\mu$g) and f-NHS (2.25 $\mu$mol) are reacted in 0.1M sodium borate (75 $\mu$l) for 4 hours at room temperature. The ssDNA is purified by ethanol precipitation, G-25 chromatography and polyacrylamide electrophoresis. The oligomer contains 1 fluorescein per oligomer.

N[(N-fluoresceinyl-6-carboxyl)-2-aminoethyl]-carboxamidyl-polymaleic acid

This polymer is comprised of multiple fluoresceins linked to a polymeric backbone and separated from each other by at least one carboxylate anion. It is prepared as follows.

Polymaleic anhydride (5 mg) in DMF (50 $\mu$l) and diaminoethane (1M in DMF, 50 $\mu$l) are added to 0.4M sodium bicarbonate (1.0 ml). After reacting at room temperature for 5 hours, the mixture is concentrated to dryness and chromatographed on G-25 by eluting with water. The excluded material is concentrated and redissolved in 0.1M sodium borate (300 $\mu$l) and reacted with 200 mM f-NHS in DMF (50 $\mu$l). The reaction mixture is concentrated and chromatographed 3 times over G-25 collecting the excluded material. After this time, silica gel thin layer chromatography reveals no unreacted fluorescein.

Fluorescence Emission of Polufluoresceinated Polymers

Solutions of 6-carboxyfluorescein(monomer) are prepared in borate buffer(pH 9.2) at various concentrations. The fluorescent emission intensities of each solution are read at 550 nm(exciting at 360 nm and 495 nm) using a Perkin-Elmer LS-5 spectrofluorimeter. A fluorescein concentration of 0.1 uM is within the range at which fluorescein emission of the monomer increases linearly with fluorescein concentration, and is thus free of effects due to intermolecular concentration quenching. This concentration is chosen as the fluorescein concentration to be used for the following comparisons.

Each of the fluoresceinated polymers, prepared as described above, are dissolved in borate buffer(pH 9.2) to a final fluorescein concentration of 0.1 uM. Fluorescence emission of these solutions and of the 0.1 uM 6-carboxyfluorescein solution are then read using the procedure described above. The fluorescence emission per fluorescein of each polymer is normalized relative to the fluorescent emission of the 6-carboxyfluorescein and the resultant data are reported in Table 1.

TABLE 1

Relative Fluorescence per Fluorescein of Polyfluoresceinated Polymers

| Compound | Excitation Wavelength (nm) | |
|---|---|---|
| | 360 | 495 |
| 6-carboxyfluorescein | 1.00 | 1.00 |
| fluoresceinated BSA | 0.25 | 0.62 |
| fluoresceinated dsDNA | 0.68 | 0.47 |
| fluoresceinated oligonucleotide | 0.82 | 0.68 |
| fluoresceinated polymaleic acid | 1.00 | 1.00 |
| fluoresceinated polyethyleneimine | 0.03 | 0.03 |

As can be seen from the results reported in Table 1, the emission of fluorescein attached to an uncharged polymer (fluoresceinated polyethyleneimine) is significantly quenched. The intermediate quenching value of fluorescein BSA is attributable to a separation of the attached fluoresceins imposed by the tertiary structure of the protein. Fluorescein attached to a polymer in which fluorescein moieties are separated by proximate negative charges (fluorescein polymaleic acid, fluorescein oligonucleotides and fluorescein dsDNA) are substantially unquenched.

EXAMPLE 2

The experiments reported by this example provide for the synthesis of (N-(fluoresceinyl-6-carboxyl)-2-aminoethyl) (N-hydroxysuccinimidyl carboxymethyl) phosphate. This reagent reacts with amines to covalently attach fluorescein by way of a negatively charged phosphodiester linkage group.

N-Trifluoroacetyl-2-aminoethyl phosphate (1)

The title compound is prepared as follows. First, 2-aminoethylphosphate (0.56 g, 4 mmol) is suspended in trifluoroacetic anhydride (2.8 ml, 20 mmol) and stirred at 0° C. for 3 hours. The resultant solution is evaporated to 1.04 g of clear oil which is used without subsequent purification.

9-Anthryl glycolate (2)

A suspension of 9-chloromethyl anthracene (1.0 g, 4.4 mmol) in dry acetonitrile (50 ml) is added to a solution of glycolic acid (0.71 g 18.8 mmol) (dried by successive evaporation from dry acetonitrile) in acetonitrile (10 ml). The reaction is stirred for 18 hours at room temperature and refluxed for 2 hours. After evaporation of acetonitrile the residue is redissolved in methylene chloride and extracted with water and 0.5M sodium bicarbonate. The solution is dried and solvent evaporated. The residue is recrystallized from refluxing benzene at 40° C. to yield 0.73 g (2.6 mmol) of yellow crystals.

((N-trifluoroacetyl)-2-aminoethyl) (9-methylanthrylcarboxymethyl) phosphate(3).

Dry Compound 2 (0.54 g, 7.0 mmol) and dry Compound 1 (0.26 g, 1.0 mmol) are dissolved in a solution of 2,4,6-triisopropylbenzene sulphonyl chloride (0.90 g. 3.0 mmol) in 20 ml dry pyridine. After 3 hours at room temperature 0.20 ml of water are added to the reaction. The reaction mixture is concentrated by evaporation. The residue is redissolved in 20 ml water and chromatographed on Dowex® 1-x8 eluting with 1.5M ammonium acetate.

(2-aminoethyl) (carboxymethyl) phosphate (4)

Compound 3(0.2 g, 0.44 mmol) and sodium methyl mercaptide (31 mg. 0.45 mmol) are dissolved in 1 ml dry DMF and reacted at room temperature under argon. After addition of 1M hydrochloric acid, the solvent is evaporated. The residue is redissolved in 10 ml water and chromatographed on Dowex® 1-x8 eluting with 1M ammonium hydroxide.

(N-(fluoroceinyl-6-carboxyl)-2-aminoethyl) (carboxymethyl) phosphate (5)

Here, 6-carboxyfluorescein-N-hydroxysuccinimide ester (0.374 g, 0.1 mmol) dissolved in 10 ml dry DMF is added to compound 4 (0.10 g, 0.5 mmol) dissolved in 0.1M sodium borate (30 ml). After 30 minutes at room temperature the reaction is evaporated to dryness and redissolved in 20 ml water. The mixture is dryness and redissolved in 20 ml water. The mixture is chromatographed on Dowex® 1-x8, eluting with 1.0M ammonium hydroxide.

(N-fluoresceinyl-6-carboxyl)-2-aminoethyl) (N-hydroxysuccinimidyl carboxymethyl) phosphate (6)

Compound (5) (0.2 g, 42 mmol), and N-hydroxysuccinimide (48 mg, 0.42 mmol) are dissolved in 5 ml dry DMF. Dicyclohexylcarbodiimide (65 mg, 42 mmol) is added and the solution is reacted overnight at room temperature. The reaction is cooled to −20° C. and filtered. The filtrate is evaporated to dryness and the oil triturated with dry toluene.

EXAMPLE 3

The experiments reported by this example provide for the synthesis of N-(fluoresceinyl-6-carboxyl)-N'-(N-hydroxysuccinimidyl succinoyl)-N-methyl-1,3-propanediamine. This reagent reacts with amines to covalently attach fluorescein by way of a positively charged tertiary amine linkage group.

N-(3-aminopropyl)-N-(fluoresceinyl-6-carboxyl)-N-methyl 1,3-propanediamine (7)

Here, 6-carboxyfluorescein-N-hydroxysuccinimide ester (0.75 g, 2 mmol) dissolved in 30 ml dry DMF is added to a solution of N-(3-aminopropyl)-N-methyl-1,3-propane diamine (1.3 ml, 8 mmol) dissolved in 1M sodium borate (250 ml). After 30 minutes at room temperature the reaction is evaporated to dryness and redissolved in 40 ml water and adjusted to pH 5 with 1M hydrochloric acid. The mixture is extracted into ethylacetate and the extracts dried over magnesium sulfate. The solvent is evaporated and the product is used without further purification.

N-(fluoresceinyl-6-carboxyl)-N-(carboxysuccinoyl)-N-methyl-1,3-propanediamine (8)

Compound 7 (206 mg, 1 mmol) dissolved in DMF (10 ml) is added to a solution of succinic anhydride (200 mg. 2 mmol) dissolved in 0.2M sodium borate (10 ml) and reacted at room temperature for 40 hours. The reaction is evaporated to dryness and the residue taken up in 10 ml water. After titration to pH 5.0, the product is collected by filtration and washed with water.

N-(fluoresceinyl-6-carboxyl)-N-(N-hydroxysuccimidyl (varboxysuccinoyl)-N-methyl-1,3-propandiamine (9)

Compound 8 (243 mg, 0.5 mmol) and N-hydroxysuccinimide (58 mg, 0.5mmol) are dissolved in dry DMF (5 ml). Dicyclohexylcarbodiimide (103 mg, 0.5 mmol) is added and the reaction allowed to proceed overnight at room temperature in the dark. After cooling to −20° C. and filtration, the solution is evaporated to dryness. The residual oil is triturated with toluene.

EXAMPLE 4

This describes reaction of the charged, linkage group-bound fluorescein NHS Compounds (6) and (9) with an amine-containing polymer.

Reaction of Compounds 6 & 9 with Polyethyleneimine

Compound 6 or 9 (20 mg/ml in DMF, 10 ul), dissolved in DMF (50 ul), is added to a solution of polyethylenamine (average molecular weight 1200; 1.5 mg/ml in 0.1M sodium borate; 300 ul). After 1 hour at room temperature, the precipitate is collected by centrifugation and purified by successively dissolving in DMF, acetic acid and reprecipitating with acetone.

What is claimed is:

1. A compound comprising:
   (i) a specific binding partner for an analyte, wherein said specific binding partner is comprised of individual monomeric units and is selected from tile group consisting of an oligonucleotide, a polynucleotide, a protein, and a saccharide; and
   (ii) a plurality of polymers, each polymer comprising a plurality of self-quenching emitter moieties alternating with a plurality of isocharged functionalities, wherein the polymers are substituted into the monomeric units of the specific binding partner, said isocharged functionalities repelling each other and said emitter moieties to an extent sufficient to inhibit self-quenching of said emitter moieties; wherein the monomers of the specific binding partner are covalently bound directly to the polymers or through linkage groups, in a manner which does not substantially inhibit specific binding between the analyte and the specific binding partner and which does not substantially interfere with the energy emission of the emitter moieties.

2. The compound of claim 1 wherein the emitter moieties are bound to the monomers of the specific binding partner through linkage groups.

3. The compound of claim 2 wherein the linkage groups include isocharged functionalities.

4. The compound of any of claims 1, 2 or 3, wherein the self-quenching emitter moieties are selected from the group consisting of fluorescers, phosphorescers, chemiluminescers, dyes or radioactive compounds.

5. The compound of claim 4 wherein the fluorescer is fluorescein.

6. The compound of any of claims 1, 2 or 3 wherein the isocharged functionalities are negatively charged.

7. The compound of any of claims 1, 2 or 3 wherein the isocharged functionalities are positively charged.

8. A compound comprising:
   (i) a specific binding partner for an analyte, wherein said specific binding partner is comprised of individual monomeric units and is selected from the group consisting of an oligonucleotide, a polynucleotide, a protein, and a saccharide; and
   (ii) a plurality of first polymers carrying self-quenching emitter moieties and a plurality of second polymers carrying a plurality of isocharged functionalities, wherein the first and second polymers are substituted into the monomeric units of the specific binding partner to form an alternating sequence of first and second polymers, said isocharged functionalities repelling each other and said emitter moieties to an extent sufficient to inhibit self-quenching of said emitter moieties; wherein the monomers of the specific binding partner are covalently bound directly to the polymers or through linkage groups, in a manner which does not substantially inhibit specific binding between the analyte and the specific binding partner and which does not substantially interfere with the energy emission of the emitter moieties.

9. The compound of claim 8 wherein the polymers are bound to the monomers of the specific binding partner through linkage groups.

10. The compound of claim 8 or 9, wherein the self-quenching emitter moieties are selected from the group consisting of fluorescers, phosphorescers, chemiluminescers, dyes or radioactive compounds.

11. The compound of claim 10 wherein the fluorescer is fluorescein.

12. The compound of claim 8 or 9 wherein the isocharged functionalities are negatively charged.

13. The compound of claim 8 or 9 wherein the isocharged functionalities are positively charged.

* * * * *